United States Patent [19]
Sutherland et al.

[11] Patent Number: 5,185,456
[45] Date of Patent: Feb. 9, 1993

[54] MACROLIDE COMPOUNDS

[75] Inventors: Derek R. Sutherland, Chalfont St Giles; Michael V. J. Ramsay, South Harrow; Edward P. Tiley, Village Way; John B. Ward, Bushey; Neil Porter, Pinner; Hazel M. Noble, Burnham; Richard A. Fletton, Ruislip; David Noble, Burnham; Brian M. Bain, Tylers Green, all of England

[73] Assignee: American Cyanamid Company, Stamford, Conn.

[21] Appl. No.: 670,770

[22] Filed: Mar. 18, 1991

Related U.S. Application Data

[63] Continuation of Ser. No. 24,762, Mar. 11, 1987, abandoned.

[30] Foreign Application Priority Data

Mar. 12, 1986 [GB] United Kingdom ............... 8606106
Mar. 12, 1986 [GB] United Kingdom ............... 8606109
Oct. 29, 1986 [GB] United Kingdom ............... 8625856
Oct. 29, 1986 [GB] United Kingdom ............... 8625862

[51] Int. Cl.$^5$ .................................... C07D 313/00
[52] U.S. Cl. .................................... 546/264
[58] Field of Search ................... 549/264; 514/450

[56] References Cited

U.S. PATENT DOCUMENTS

| 4,457,920 | 7/1984 | Mrozik ............... 549/264 |
| 4,547,520 | 10/1985 | Ide et al. ............ 549/264 |
| 4,579,864 | 4/1986 | Linn et al. ........... 549/264 |
| 4,978,675 | 12/1990 | Ward et al. ........... 549/264 |

FOREIGN PATENT DOCUMENTS 0170006 2/1986 European Pat. Off. .

Primary Examiner—Alan L. Rotman
Assistant Examiner—Ba K. Trinh
Attorney, Agent, or Firm—Bacon & Thomas

[57] ABSTRACT

Compounds of formula (I)

and salts thereof wherein
$R^1$ is a methyl, ethyl or isopropyl group;
$R^2$ is a hydrogen atom or a group $OR^4$ (where $OR^4$ is a hydroxyl group or a substituted hydroxyl group having up to 25 carbon atoms) and $R^3$ is a hydrogen atom, or (when $R^2$ is a hydrogen atom) a bromine atom; or $R^2$ and $R^3$ together with the carbon atom to which they are attached represent $>C=CH_2$, $>C=O$ or $>C=NOR^5$ (where $R^5$ is a hydrogen atom, a $C_{1-8}$ alkyl group or a $C_{3-8}$ alkenyl group and the group $>C=NOR^5$ is in the E configuration); and
Y represents an oxygen atom or a group $NOR^5$ (where $R^5$ is as defined above); with the proviso that when Y is an oxygen atom and $R^1$ is an isopropyl group, then $R^2$ is other than hydroxyl group.

These compounds may be used for controlling insect, acarine, nematode or other pests.

1 Claim, No Drawings

MACROLIDE COMPOUNDS

This application is a continuation of application Ser. No. 07/024,762, filed Mar. 11, 1987, now abandoned.

This invention relates to new antibiotic compounds and to processes for their preparation.

In our United Kingdom Patent Specification No. 2166436A we describe the production of Antibiotics S541 which may be isolated from the fermentation products of a novel Streptomyces sp. having an accession No. NC1B12015.

We have now found a further group of compounds with antibiotic activity which may be prepared by chemical modification of Antibiotics S541. The novel compounds of the invention have antibiotic activity and/or are of use as intermediates in the preparation of other active compounds.

Thus, in one aspect, the invention provides the compounds of formula (I):

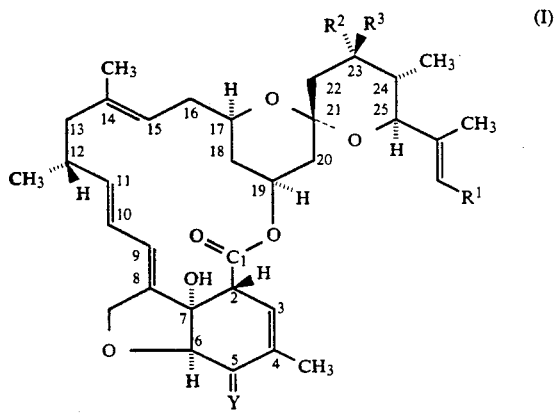

and salts thereof wherein $R^1$ is a methyl, ethyl or isopropyl group;

$R^2$ represents a hydrogen atom or a group $OR^4$ (where $OR^4$ is a hydroxyl group or a substituted hydroxyl group having up to 25 carbon atoms) and $R^3$ represents a hydrogen atom, or $R^2$ and $R^3$ together with the carbon atom to which they are attached represent $>C=CH_2$, $>C=O$ or $>C=NOR^5$ (where $R^5$ represents a hydrogen atom, a $C_{1-8}$ alkyl group or a $C_{3-8}$ alkenyl group and the group $>C=NOR^5$ is in the E configuration) or when $R^2$ represents a hydrogen atom then $R^3$ may also represent a bromine atom; and Y represents an oxygen atom or a group $NOR^5$ (where $R^5$ is as defined above); with the proviso that when Y represents an oxygen atom and $R^1$ represents an isopropyl group then $R^2$ cannot represent a hydroxyl group.

When the compounds of formula (I) are to be used as intermediates, the group $R^2$ will often be a protected hydroxy group and the invention particularly includes such protected compounds.

Salts that may be formed with compounds of formula (I) containing an acidic group include salts with bases e.g. alkali metal salts such as sodium and potassium salts.

When the groups $R^2$ in compounds of formula (I) is a substituted hydroxyl group it may be an acyloxy group [e.g. a group of the formula —$OCOR^6$, —$OCO_2R^6$ or —$OCSOR^6$ (where $R^6$ is an aliphatic, araliphatic or aromatic group, for example an alkyl, alkenyl, alkynyl, cycloalkyl, aralkyl or aryl group)], a formyloxy group, a group —$OR^7$ [where $R^7$ is as defined above for $R^6$], a group —$OSO_2R^8$ [where $R^8$ is a $C_{1-4}$ alkyl or $C_{6-10}$ aryl group), a silyloxy group, a cyclic or acyclic acetaloxy group, a group $OCO(CH_2)_nCO_2R^9$ (where $R^9$ is a hydrogen atom or a group as defined for $R^6$ above and n represents zero, 1 or 2) or a group $R^{10}R^{11}NCO_2$ (where $R^{10}$ and $R^{11}$ may each independently represent a hydrogen atom or a $C_{1-4}$ alkyl group).

Where $R^6$ or $R^7$ are alkyl groups, they may be for example $C_{1-8}$ alkyl groups e.g. methyl, ethyl, n-propyl, i-propyl, n-butyl, i-butyl, t-butyl or n-heptyl which alkyl groups may also be substituted. Where $R^7$ is a substituted alkyl group it may be substituted by, for example, one or more, e.g. two or three halogen atoms (e.g. chlorine or bromine atoms), or a carboxy, $C_{1-4}$ alkoxy (e.g. methoxy, ethoxy), phenoxy or silyloxy group. Where $R^7$ is a substituted alkyl group it may be substituted by one or more halogen atoms (e.g. chlorine or bromine atoms, or a $C_{1-4}$ alkoxy (e.g. methoxy or ethoxy) or cycloalkyl e.g. cyclopropyl group.

Where $R^6$ or $R^7$ are alkenyl or alkynyl groups, they may be for example $C_{2-8}$ alkenyl, e.g. allyl, or $C_{2-8}$ alkynyl groups.

Where $R^6$ or $R^7$ are cycloakyl groups, they may be for example $C_{3-12}$ cycloalkyl, such as $C_{3-7}$ cycloalkyl, e.g. cyclopentyl groups.

Where $R^6$ or $R^7$ are aralkyl groups, they preferably have 1 to 6 carbon atoms in the alkyl moiety and the aryl group(s) may be carbocyclic or heterocyclic and preferably contain 4–15 carbon atoms e.g. phenyl. Examples of such groups include phen$C_{1-6}$alkyl, e.g. benzyl groups.

Where $R^6$ or $R^7$ are aryl groups, they may be carbocyclic or heterocyclic and preferably have 4–15 carbon atoms, and may be for example a phenyl group.

When $R^2$ is a group —$OSO_2R^8$, it may be for example a methylsulphonyloxy or p-toluenesulphonyloxy group.

Where $R^2$ represents a cyclic acetaloxy group, it may for example have 5–7 ring members and may be for example a tetrahydropyranyloxy group.

When $R^2$ represents a silyloxy group or $R^6$ contains a silyloxy substituent, the silyl group may carry three groups which may be the same or different, selected from alkyl, alkenyl, alkoxy, cycloalkyl, aralkyl, aryl and aryloxy groups. Such groups may be as defined above for $R^6$ and particularly include methyl, t-butyl and phenyl groups. Particular examples of such silyloxy groups are trimethylsilyloxy and t-butyldimethylsilyloxy.

When $R^2$ represents a group —$OCO(CH_2)_nCO_2R^9$ it may for example be a group $OCOCO_2R^9$ or $OCOCH_2CH_2CO_2R^9$ where $R^9$ represents a hydrogen atom or a $C_{1-4}$ alkyl (e.g. methyl or ethyl) group.

When $R^2$ represents a group $R^{10}R^{11}NCO_2$-, $R^{10}$ and $R^{11}$ for example may each independently represent a hydrogen atom or a methyl or ethyl group.

When $R^5$ represents a $C_{1-8}$ alkyl group, it may be for example a methyl, ethyl, n-propyl, n-butyl, i-butyl or t-butyl, group, and is preferably a methyl group.

When $R^5$ represents a $C_{3-8}$ alkenyl group, it may be for example an allyl group.

An important group of compounds of formula (I) is that in which $R^1$ represents a methyl, ethyl or isopropyl group, $R^2$ represents a group $OR^4$ (where $OR^4$ is a hydroxy group or a substituted hydroxy group having up to 25 carbon atoms) and $R^3$ represents a hydrogen atom. Such compounds in which $R^2$ represents a hydroxy, acetoxy or ethoxy group are particularly preferred.

Another important group of compounds of formula (I) is that in which $R^1$ represents a methyl, ethyl or isopropyl group and $R^2$ and $R^3$ together with the carbon atom to which they are attached form a group $>C=CH_2$.

A further important group of compounds of formula (I) is that in which $R^1$ represents a methyl, ethyl or isopropyl group and $R^2$ and $R^3$ is each a hydrogen atom.

Another important group of compounds of formula (I) is that in which $R^1$ is a methyl, ethyl or isopropyl group and $R^2$ and $R^3$ together with the carbon atom to which they are attached form a group $>C=NOCH_3$.

Yet another important group of compounds of formula (I) is that in which $R^1$ is a methyl, ethyl or isopropyl group and $R^2$ and $R^3$ together with the carbon atom to which they are attached form a group $>C=O$.

In the compounds of formula (I), the group $R^1$ is preferably an isopropyl group.

Particularly important compounds of formula (I) are those in which:

$R^1$ represents an isopropyl group, $R^2$ and $R^3$ together with the carbon atom to which they are attached represent $>C=NOCH_3$ and Y represents an oxygen atom.

$R^1$ represents an isopropyl group, $R^2$ and $R^3$ together with the carbon atom to which they are attached represent $>C=O$ and Y represents an oxygen atom; and $R^1$ represents an isopropyl group, $R^2$ and $R^3$ together with the carbon atom to which they are attached represent $>C=NOCH_3$ and Y represents a group $NOCH_3$.

As indicated previously, the compounds according to the invention may be of use as antibiotics and/or as intermediates for the preparation of other active compounds. When the compounds of the invention are to be used as intermediates, the $R^2$ group may be a protected hydroxyl group. It will be appreciated that such a group should have the minimum of additional functionality to avoid further sites of reaction and should be such that it is possible to selectively regenerate a hydroxyl group from it. Examples of protected hydroxyl groups are well known and are described, for example, in "Protective Groups in Organic Synthesis" by Theodora W. Greene. (Wiley-Interscience, New York 1981) and "Protective Groups in Organic Chemistry" by J F W McOmie (Plenum Press, London, 1973). Examples of $R^2$ protected hydroxy groups include phenoxyacetoxy, silyloxyacetoxy, (e.g. trimethylsilyloxyacetoxy and t-butyldimethylsilyloxyacetoxy), and silyloxy such as trimethylsilyloxy and t-butyldimethylsilyloxy. Compounds of the invention containing such groups will primarily be of use as intermediates. Other groups, such as acetoxy, may serve as protected hydroxyl groups, but may also be present in final active compounds.

Compounds of the invention have antibiotic activity e.g. antihelminthic activity, for example against nematodes, and in particular, anti-endoparasitic and anti-ectoparasitic activity.

The compounds of the invention are therefore of use in treating animals and humans with endoparasitic and/or ectoparasitic infections.

Ectoparasites and endoparasites infect humans and a variety of animals and are particularly prevalent in farm animals such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

The compounds according to the invention have been found to be effective both in vitro and in vivo against a range of endoparasites and ectoparasites. The antibiotic activity of compounds of the invention may, for example, be demonstrated by their activity against free living nematodes e.g. *Caenorhabiditis elegans*. In particular, we have found that compounds of the invention are active against parasitic nematodes such as *Nematospiroides dubius* and *Nippostrongylus braziliensis*.

Compounds of the invention are also of use as antifungals, for example, against strains of *Candida* sp. such as *Candida albicans* and *Candida glabrata* and against yeast such as *Saccharomyces carlsbergenis*.

Compounds of the invention are also of use in combating insect, acarine and nematode pests in agriculture, horticulture, forestry, public health and stored products. Pests of soil and plant crops, including cereals (e.g. wheat, barley, maize and rice), cotton, tobacco, vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Nephotettix cincticeps, Nilparvata lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla; Thrips tabaci*; cockroaches such as *Blatella germanica* and *Periplaneta americana* and mosquitoes such as *Aedes aegypti*.

According to the invention we therefore provide compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or vegetation) or a locus thereof or to the pests themselves.

Compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds according to the invention may be formulated for use in veterinary or human medicine by injection and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use. Oily vehicles include polyhydric alcohols and their esters such as glycerol esters, fatty acids, vegetable oils such as arachis oil or cottonseed oil, mineral oils such as liquid paraffin, and ethyl oleate and other similar compounds. Other vehicles such as propylene glycol may also be used.

Compositions for veterinary medicine may also be formulated as intramammary preparations in either long acting or quick-release bases and may be sterile solutions or suspensions in aqueous or oily vehicles optionally containing a thickening or suspending agent such as soft or hard paraffins, beeswax, 12-hydroxy stearin, hydrogenated castor oil, aluminium stearates, or glyceryl monostearate. Conventional non-ionic, cationic or anionic surface active agents may be used alone or in combination in the composition.

The compounds of the invention may also be presented for veterinary or human use in a form suitable for oral administration, for example in the form of solutions, syrups or suspensions, or a dry powder for constitution with water or other suitable vehicle before use, optionally with flavouring and colouring agents. Solid compositions such as tablets, capsules, lozenges, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form. Examples of suitable pharmaceutically acceptable carriers for use in solid dosage forms include binding agents (e.g. pregelatinised maize starch, polyvinylpyrrolidone or hydroxypropyl methylcellulose); fillers (e.g. lactose, micro-crystalline cellulose or calcium phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art.

Examples of suitable pharmaceutically acceptable additives for use in liquid dosage forms include suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid); stabilising and solubilising agents may also be includeed.

Pastes for oral administration may be formulated according to methods well known in the art. Examples of suitable pharmaceutically acceptable additives for use in paste formulations include suspending or gelling agents e.g. aluminium distearate or hydrogenated castor oil; dispersing agents e.g. polysorbates, non-aqueous vehicles e.g. arachis oil or oily esters; stabilising and solubilising agents. The compounds of the invention may also be administered in veterinary medicine by incorporation thereof into animals daily solid or liquid dietary intake, e.g. as part of the daily animal feed or drinking water.

The compounds of the invention may also be administered orally in veterinary medicine in the form of a liquid drench such as a solution, suspension or dispersion of the active ingredient together with a pharmaceutically aceptable carrier or excipient.

The compounds of the invention may also, for example, be formulated as suppositories e.g. containing conventional suppository bases for use in veterinary or human medicine or as pessaries e.g. containing conventional pessary bases.

Compounds according to the invention may be formulated for topical administration, for use in veterinary and human medicine, as ointments, creams, lotions, shampoos, powders, pessaries, sprays, dips, aerosols, drops (e.g. eye or nose drops) or pour-ons. Ointments and cream may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents e.g. stabilising and solubilising agents.

Lotions may be formulated with an aqueous or oily base and will in general also contain one or more emulsifying agents, stabilising agents, dispersing agents, suspending agents, thickening agents, or colouring agents.

Powders may be formed with the aid of any suitable powder base. Drops may be formulated with an aqueous or non aqueous base also comprising one or more dispersing agents, stabilising agents, solubilising agents or suspending agents. They may also contain a preservative.

For topical administration by inhalation the compounds according to the invention may be delivered for use in veterinary or human medicine in the form of an aerosol spray presentation or an insufflator.

The compounds of the invention may be administered in combination with other pharmaceutically active ingredents.

The total daily dosages of compounds of the invention employed in both veterinary and human medicine will suitably be in the range 1–2000 $\mu$g/kg bodyweight, preferably from 50–1000 $\mu$g/kg and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Such formulations are well known in the art and may be prepared by conventional methods such as, for example by blending and/or grinding of the active ingredient(s) together with the carrier or diluent, e.g. solid carrier, solvent or surface active agent.

Suitable solid carriers, for use in the formulations such as dusts, granulates and powders may be selected from for example natural mineral fillers, such as diatomite, talc, kaolinite, montmorillonite prophyllite or attapulgite. Highly dispersed silicic acid or highly dispersed absorbent polymers may, if desired, be included in the composition. Granulated adsorptive carriers which may be used may be porous (such as pumice, ground brick, sepiolite or bentonite) or non-porous (such as calcite or sand). Suitable pregranulated materials which may be used and which may be organic or inorganic include dolomite and ground plant residues.

Suitable solvents for use as carriers or diluents include aromatic hydrocarbons, aliphatic hydrocarbons, alcohols and glycols or ethers thereof, esters, ketones, acid amides, strongly polar solvents, optionally epoxidized vegetable oils and water.

Conventional non-ionic, cationic or anionic surface-active agents, e.g. ethoxylated alkyl phenols and alcohols, alkali metal or alkaline earth metal salts of alkyl benzene sulphonic acids, lignosulphonic acids or sulphosuccinic acids or sulphonates of polymeric phenols which have good emulsifying, dispersing and/or wetting properties may also be used either alone or in combination in the compositions.

Stabilizers, anti-caking agents, anti-foaming agents, viscosity regulators, binders and adhesives, photostabilisers as well as fertilizers, feeding stimulants or other active substances may, if desired, be included in the compositions. The compounds of the invention may also be formulated in admixture with other insecticides, acaricides and nematicides.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The compounds of the invention may be prepared by the processes discussed below. In some of these processes it may be necessary to protect a hydroxyl group at the 23-position in the starting material prior to effecting the reaction described. In such cases it may then be necessary to deprotect the same hydroxyl group once the reaction has occurred to obtain the desired compound of the invention. Conventional protection and deprotection methods may be used, for example as described in the aforementioned books by Greene and McOmie.

The compounds of the invention in which Y represents an oxygen atom may be produced by oxidation of the corresponding 5-hydroxy compounds. The starting materials are thus compounds of formula (II):

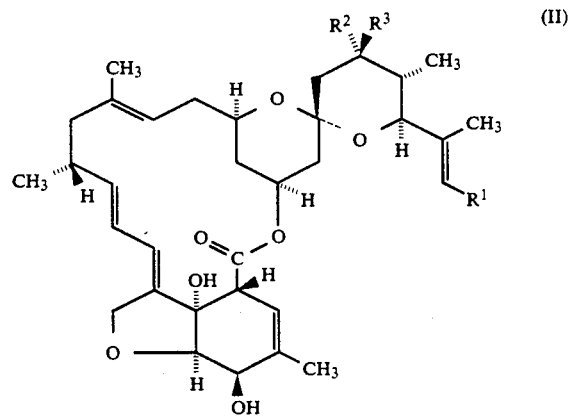

(where $R^1$, $R^2$ and $R^3$ are as previiously defined in formula (I)). The reaction may be effected with an oxidising agent serving to convert an allylic secondary hydroxyl group to an oxo group, whereby a compound of formula (I) is produced.

Suitable oxidising agents include, for example, transition metal oxides, such as manganese dioxide, and atmospheric oxygen in the presence of a suitable catalyst such as a finely divided metal e.g. platinum.

The oxidising agent will generally be used in excess over the stoichiometric quantity.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate. Combinations of such solvents either alone or with water may also be used.

The reaction may be carried out at a temperature of from $-50°$ C. to $+50°$ C., preferably from 0° to 30° C.

The compounds of formula (I) in which $R^2$ is a substituted hydroxyl group may also be prepared by reacting the corresponding compound of formula (I) in which $R^2$ is a hydroxyl group with reagents serving to form a substituted hydroxyl group. The reaction will in general be an acylation, formylation, sulphonylation, etherification, silylation or acetal formation.

Thus, for example, acylation may be effected using an acylating agent such as an acid of formula $R^6COOH$ or a reactive derivative thereof, such as an acid halide (e.g. acid chloride), anhydride or activated ester, or a reactive derivative of a carbonic acid $R^6OCOOH$ or thiocarbonic acid $R^6OCSOH$.

Acylations employing acid halides and anhydrides may if desired be effected in the presence of an acid binding agent such as a tertiary amine (e.g. triethylamine, dimethylaniline or pyridine), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acylations employing acids are desirably conducted in the presence of a condensing agent, for example a carbodiimide such as N,N'-dicyclohexylcarbodiimide or N-ethyl-N'γ-dimethylaminopropylcarbodiimide; a carbonyl compound such as carbonyldiimidazole; or an isoxazolium salt such as N-ethyl-5-phenylisoxazolium perchlorate.

An activated ester may conveniently be formed in situ using, for example, 1-hydroxybenzotriazole in the presence of a condensing agent as set out above. Alternatively, the activated ester may be preformed.

The acylation reaction may be effected in aqueous or non-aqueous reaction media, conveniently at a temperature in the range $-20°$ to $+100°$ C., e.g. $-10°$ to $+50°$ C.

Formylation may be effected using an activated derivative of formic acid e.g. N-formyl imidazole or formic acetic anhydride under standard reaction conditions.

Sulphonylation may be effected with a reactive derivative of a sulphonic acid $R^8SO_3H$ such as a sulphonyl halide, for example a chloride $R^8SO_2Cl$ or a sulphonic anhydride. The sulphonylation is preferably effected in the presence of a suitable acid binding agent as described above.

Etherification may be effected using a reagent of formula $R^7Y$ (where $R^7$ is as previously defined and Y represents a leaving group such as chlorine, bromine or iodine atom or a hydrocarbylsulphonyloxy group, such as mesyloxy or tosyloxy, or a haloalkanoyloxy group such as dichloroacetoxy). The reaction may be effected in the presence of a silver salt such as silver oxide, silver perchlorate, silver carbonate or silver salicylate or mixtures thereof, and this system may be particularly appropriate when etherification is carried out using an alkyl halide (e.g. methyl iodide).

Etherification may conveniently be effected in a solvent such as an ether e.g. diethyl ether.

Acetal formation may be carried out by reaction with a cyclic or acyclic vinyl ether. This method is especially useful for production of tetrahydropyranyl ethers, using dihydropyran as reagent, or 1-alkoxyalkyl ethers such as 1-ethoxyalkyl ether, using an alkyl vinyl ether as reagent. The reaction is desirably carried out in the presence of a strong acid catalyst, for example a mineral acid such as sulphuric acid, or an organic sulphonic acid such as p-toluene sulphonic acid, in a non-hydroxylic, substantially water-free solvent.

Solvents which may be employed in the above reactions include ketones (e.g. acetone), amides (e.g. N,N-dimethylformamide, N,N-dimethylacetamide or hexamethylphosporamide), ethers (e.g. cyclic ethers such as tetrahydrofuran or dioxan, and acyclic ethers such as dimethoxyethane or diethylether), nitriles (e.g. methylene chloride), and esters such as ethyl acetate, as well as mixtures of two or more such solvents.

Silylation may be effected by reaction with a silyl halide (e.g. chloride), advantageously in the presence of a base such as imidazole triethylamine or pyridine, using a solvent such as dimethylformamide.

In a further process according to the invention a compound of formula (I) in which $R^2$ represents a hydrogen atom and $R^3$ represents a bromine atom may be prepared from the corresponding compound of formula (I) in which $R^2$ represents a hydroxyl group and $R^3$ represents a hydrogen atom.

The reaction is effected using a brominating agent able to perform the displacement with inversion of configuration. Suitable brominating agents include triarylphosphine dibromides such as triphenylphosphine dibromide.

The reaction is conveniently carried out in a solvent e.g. a nitrile such as acetonitrile at a temperature in the range of 0° to 50° C., conveniently at room temperature.

In another process according to the invention a compound of formula (I) in which $R^2$ and $R^3$ together with the carbon atom to which they are attached represent $>C=NOR^5$, Y represents an oxygen atom and $R^1$ is as defined in formula (I), or $R^2$ represents a hydrogen atom or a group $OR^4$ and $R^3$ represents a hydrogen atom or $R^2$ and $R^3$ together with the carbon atom to which they are attached represent $>C=CH_2$ or $>C=NOR^5$, Y represents a group $NOR^5$ and $R^1$ is as defined in formula (I) may be prepared from the corresponding 5 and/or 23-keto compound of formula (I) by reaction with a reagent $H_2NOR^5$ (where $R^5$ is as previously defined).

In one embodiment of the process, a compound of formula (I) in which $R^2$ and $R^3$ together with the carbon atom to which they are represent $>C=NOR^5$ may be prepared from a corresponding compound of formula (I) in which $R^2$ and $R^3$ together with the carbon atom to which they are attached represent $>C=O$.

In a further embodiment of the process, a compound of formula (I) in which Y represents $NOR^5$ may be prepared from a corresponding compound of formula (I) in which Y represents an oxygen atom.

Compounds of formula (I) in which $R^2$ and $R^3$ together with the carbon atom to which they are attached represent $>C=NOR^5$ and Y represents $NOR^5$ may conveniently be prepared from the correspond 5,23-diketo compound of formula (I) (in which $R^1$ and $R^2$ together with the carbon atom to which they are attached represent $>C=O$ and Y is an oxygen atom) using two equivalents of the reagent $H_2NOR^5$.

The oximation reaction may conveniently be effected at a temperature in the range $-20°$ to $+100°$ C., e.g. $-10°$ to $+50°$ C. It is convenient to use the reagent $H_2NOR^5$ in the form of a salt, for example an acid addition salt such as the hydrochloride. When such a salt is employed the reaction may be carried out in the presence of an acid binding agent.

Solvents which may be employed include alcohols (e.g. methanol or ethanol), amides (e.g. N,N-dimethylformamide, N,N-dimethylacetamide or hexamethylphosphoramide), ethers (e.g. cyclic cyclic ethers such as tetrahydrofuran or dioxan, and acylic ethers such as dimethoxyethane or diethylether), nitriles (e.g. acetonitrile), sulphones (e.g. sulpholane) and hydrocarbons such as halogenated hydrocarbons (e.g. methylene chloride), as well as mixtures of two or more such solvents. Water may also be employed as a cosolvent.

When aqueous conditions are employed the reaction may conveniently be buffered with an appropriate acid, base or buffer.

Suitable acids include mineral acids, such as hydrochloric or sulphuric acid, and carboxylic acid such as acetic acid. Suitable bases include alkali metal carbonates and bicarbonates such as sodium bicarbonate, hydroxides such as sodium hydroxide, and alkali metal carboxylates such as sodium acetate. A suitable buffer is sodium acetate/acetic acid.

In a further process according to the invention a compound of formula (I) in which $R^2$ and $R^3$ together with the carbon atom to which they are attached represent $>C=O$ may be prepared by oxidising a compound of formula (I) wherein $R^2$ is a hydroxyl group. The reaction may be effected with an oxidising agent serving to convert is secondary hydroxyl group to an oxo group, whereby a compound of formula (I) is produced.

Suitable oxidising agents include quinones in the presence of water, e.g. 2,3-dichloro-5,6-dicyano-1,4-benzoquinone or 2,3,5,6-tetrachloro-1,4-benzoquinone; a chromium (VI) oxidising agent, e.g. pyridinium dichromate or chromium trioxide in pyridine; a manganese (IV) oxidising agent, e.g. manganese dioxide in dichloromethane; an N-halosuccinimide, e.g. N-chlorosuccinimide or N-bromosuccinimide; a dialkylsulphoxide e.g. dimethylsulphoxide, in the presence of an activating agent such as N,N'-dicyclohexylcarbodiimide or an acyl halide, e.g. oxalyl chloride; or a pyridine-sulphur trioxide complex.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate or a substituted amide e.g. dimethylformamide. Combinations of such solvents either alone or with water may also be used.

The reaction may be carried out at a temperature of from $-80°$ C. to $+50°$ C.

Intermediates of formula (II) in which $R^2$ and $R^3$ together with the carbon atom to which they are attached represent $>C=CH_2$ may be prepared by reacting the corresponding 23-keto compounds (i.e. compounds of formula (II) in which $R^2$ and $R^3$ together with the carbon atom to which they are attached represent $>C=O$) or a 5-hydroxy protected derivative thereof with an appropriate Wittig reagent e.g. a phosphorane of formula $(R^a)_3 P=CH_2$ (where $R^a$ is $C_{1-6}$ alkyl or aryl e.g. monocyclic aryl such as phenyl). Suitable reaction solvents include ethers such as tetrahydrofuran or diethyl ether or a dipolar aprotic solvent such as dimethylsulphoxide. The reaction may be carried out at any suitable temperature e.g. at 0°. Alternatively, the 23-keto compound may be reacted with an organometallic reagent generated from $CH_2(Hal)_2$-$Zn$-$TiCl_4$ (where Hal is an iodine or bromine atom). The reaction may be performed in a solvent such as tetrahydrofuran at, for example, room temperature.

The organometallic reagent for use in this reaction may be prepared according to the methods of Hibino et al., Tet. Lett., 1985, 5579, Takai et al., Tet. Lett., 1978, 2417 and Lombardo, Tet. Lett., 1982, 4293.

Intermediates of formula (II) in which $R^2$ and $R^3$ together with the carbon atom to which they are attached represent $>C=NOR^5$ may be prepared from the corresponding 23-keto compounds of formula (II) according to the oximation process previously described.

The compounds of formula (II) in which $R^1$ is a methyl, ethyl or isopropyl group, $R^2$ is a hydrogen atom or a group $OR^4$ and $R^3$ is a hydrogen atom, or $R^2$ and $R^3$ together with the carbon atom to which they are attached represent $>C=O$ are either known compounds described in UK Patent Specification No. 2176182A or may be prepared from the known compounds using methods analogues to those described therein.

The invention is further illustrated by the following Examples. All temperatures are in °C. The compounds are hereinafter named by reference to the known parent "Factors", Factors A, C and D described in UK Patent Specification No 2166436A. Factor A is a compound of formula (II) in which $R^1$ is isopropyl, $R^2$ is hydroxy and $R^3$ is hydrogen, Factor C is a compound of formula (II) in which $R^1$ is methyl, $R^2$ is hydroxy and $R^3$ is hydrogen and Factor D is a compound of formula (II) in which $R^1$ is ethyl, $R^2$ is hydroxy and $R^3$ is hydrogen.

INTERMEDIATE 1

23-Deoxy-23-methylene Factor A

Diiodomethane (0.4 ml) was added, with stirring, to a suspension of zinc powder (0.6 g) in dry tetrahydrofuran (10 ml). The mixture was stirred at 22° for 30 min and then cooled to 0° during the addition of a dichloromethane solution of titanium tetrachloride (1.0 ml, 1.0M solution). The resulting brown mixture was stirred at 22° for 30 min. A solution of 23-keto Factor A (Example 21 in UK-2176182A) (204 mg) in dry tetrahydrofuran (3 ml) was added and stirring was contained for a further 30 min. Diethyl ether (10 ml) was added and the organic solution was washed successively with 20 ml portions of 1M-hydrochloric acid and brine. The dried solution was concentrated to give a brown glass which was purified by medium pressure chromatography using silica (Merck Kieselgel 60, 230-400 mesh, 125 g). Elution with dichloromethane:ethyl acetate (17:3) gave an impure sample of the title compound (65 mg) which was purified further by chromatography on a silica preparative plate (Merck Kieselgel 60 20 cm×20 cm×2 mm). Elution with 10:1 dichloromethane:ethyl acetate gave the title compound (47 mg) as a white foam. $\delta(CDCl_3)$ includes 4.76 (s, 1H), 4.81(s, 1H).

INTERMEDIATE 2

5-Keto Factor A

Factor A (250 mg) in ether (30 ml) was stirred with active manganese dioxide (1.0 g) for 2.75 hr. The mixture was filtered through a Kieselguhr pad, and the filtrate evaporated to give the title compound as a foam (240 mg). A portion was crystallized from petroleum-ether to give microcrystals, $\lambda_{max}$ (EtOH) 240.5 nm ($E_1^1$ 495); $\delta$ ($CDCl_3$) values 6.58 (s; 1H), 2.60 (m; 1H) 1.89 (s; 3H), 1.62 (s; 3H), 1.53 (s; 3H), 1.05 (d 6; 3H), 1.00 (d 6; 3H), 0.96 (d 6; 3H) and 0.80 (d 6; 3H); m/z include 610, 592, 574, 441 265, 247, 237, 219 and 151.

EXAMPLE 1

5,23-Diketo Factor A

An ether solution of 23-keto Factor A (130 mg) was stirred with precipitated manganese dioxide (400 mg) at 21° for 3½ h. The mixture was filtered through kieselguhr and the filter-cake washed well with ether. Evaporation of filtrate and washings provided a gum which crystallized on scratching. The crystals were washed with di-isopropylether prior to collection to afford the title compound (80 mg) m.p. ca 190° (decomp.); $[\alpha]_D^{23} +82°$ (c 0.44, $CHCl_3$; $\lambda_{max}^{EtOH}$ 241 nm ($\epsilon_{max}$ 31,600); $\gamma_{max}$ ($CHBr_3$) 3550 and 2450 (OH), 1715 (ester and $C_{23}$-ketone); 1678 cm$^{-1}$ ($\alpha,\beta$-unsaturated ketone); $\delta$ ($CDCl_3$) includes 6.57 (m, 1H); 2.50 (s, 2H); and 1.89 (m, 3H); m/z=608 (M+).

Similarly prepared were Examples 2, 3, 4 and 5.

EXAMPLE 2

5-Keto Factor C

From Factor C (258 mg) and obtained as needles (152 mg), m.p. 215 (dec.), $[\alpha]_D^{22} +94°$ (c 0.68, $CHCl_3$); $\lambda_{max}$ (EtOH) 241 nm ($\epsilon_{max}$ 32,000); $\gamma_{max}$ ($CHBr_3$) 3,500

(OH), 1710 (ester), and 1677 cm$^{-1}$ (unsaturated ketone); δ (CDCl$_3$) include 6.56 (s, 1H,), 1.89 (s, 3H), 1.68 (d 7 Hz, 3H), 1.54 (s, 3H), 1.02 (d 7 Hz, 3H) and 0.82 (d 7 Hz, 3H). m/z=582 (M+).

EXAMPLE 3

23-Acetoxy-5-keto Factor A

From 23-acetoxy Factor A (Example 11 in UK-2176182A) and obtained as microcrystalline needles. m.p. 150°-152°, $[\alpha]_D^{23}$ +110° (c 0.52, CHCl$_3$); $\lambda_{max}^{EtOH}$ 241 nm ($\epsilon_{max}$ 30,200); $\gamma_{max}$ (CHBr$_3$) 3540 and 3490 (OH), 1718 (acetate and ester) and 1678 cm$^{-1}$ α,β-unsaturated ketone); δ (CDCl$_3$) include 6.55 (m, 1H), 4.90 (q, 3 Hz, 1H), 2.03 (s, 3H) and 1.87 (m, 3H); m/z=652 (M+).

EXAMPLE 4

23Desoxy-5-keto Factor A

From 23-desoxy Factor A (Example 27 in UK-2176182A) and obtained as a foam upon chromatography over Merck Kieselgel 60, 230-400 mesh silica gel. $[\alpha]_D^{23}$ +90° (c 0.28, CHCl$_3$); $\lambda_{max}^{EtOH}$ 241 nm ($\epsilon_{max}$ 31,400); $\gamma_{max}$ (CHBr$_3$) 3480 (OH), 1710(ester) and 1678 cm$^{-1}$ (α,β-unsaturated ketone); δ (CDCl$_3$) include 6.56 (m, 1H), 1.88 (m, 3H) and 0.69 (broad d, ca 5 Hz, 3H); m/z=594 (M+).

EXAMPLE 5

5-Keto Factor D

From Factor D (240 mg) and obtained as a white solid (63 mg) after chromatography on Merck Kieselgel 60, 70-230 mesh silica (2.5 g) eluting with dichloromethane:ethyl acetate (10:1) and trituration with ether. M.p. 242°-244°, $[\alpha]_D^{21}$ +69.7° (c 0.8, CHCl$_3$); $\lambda_{max}^{EtOH}$, 241 nm ($\epsilon_{max}$ 31500); $\gamma_{max}$ (CHBr$_3$)3490(OH), 1708 (ester) and 1675 cm$^{-1}$ (conjugated ketone); δ(CDCl$_3$) 0.80 (d, 7 Hz; 3H), 0.99 (d, 6 Hz; 3H), 1.01 (t, 7 Hz; 3H), 1.51 (s; 3H), 1.60 (s; 3H), 1.87 (s; 3H), 3.54 (m; 1H), 3.65 (m; 1H), 3.77 (d, 10 Hz; 1H), 3.77 (s; 1H), 3.81(s; 1H) and 6.55 (m; 1H). m/z=596 (M+).

EXAMPLE 6

23-Desoxy-23-epi-bromo-5-keto Factor A

Bromine (0.15 ml) was added dropwise to a stirred solution of triphenylphosphine (0.74 g) in dimethylformamide (2.6 ml) under nitrogen. The suspension was allowed to cool to room temperature and was diluted with ether. The solvent was decanted off and the solid was washed with ether. The dried solid was redissolved in acetonitrile (20 ml) and an aliquot (5 ml) was cooled in an ice bath and a solution of 5-keto Factor A (100 mg) in acetonitrile (2 ml) was added under nitrogen. After 1 h the solution was allowed to warm to room temperature and the reaction was left for 20 h. The mixture was partitioned between ethyl acetate and 2N hydrochloric acid and the organic phase was separated. The organic phase was washed with 2N hydrochloric acid, then with saturated sodium bicarbonate solution, then was dried over sodium sulphate, and the solvent was evaporated. The residue was chromatographed over a column of silica (Merck Art 9385; 75 ml) made up in hexane (60°-80°)/ethyl acetate and eluted with the same solvent. Appropriate fractions of the major component were combined and the solvent was evaporated to leave the title compound as a foam (20 mg) $[\alpha]_D^{22}$ +4.3° (c 0.46; CHCl$_3$); $\lambda_{max}^{EtOH}$ 240 nm ($\epsilon$26,000); $\gamma_{max}$ (CHBr$_3$) 3500 (OH), 1710 (ester), 1678 (ketone), 997 (C-O); δ (CDCl$_3$) include 0.95 (d; 3H), 0.97 (d; 3H), 1.00 (d; 3H), 3.58 (m, 1H), 4.19 (t;d; 1H), 3.83 (s; 1H), 3.85 (s; 1H), and 6.58 (m; 1H).

EXAMPLE 7

5-Keto Factor A 23-ethyl ether

A solution of 5-keto Factor A (350 mg) in dry ether (15 ml) was treated at 20°, under nitrogen, with silver carbonate (785 mg), iodoethane (0.27 ml) and silver perchlorate (590 mg). The resulting suspension was stirred for 64 h under nitrogen, diluted with ethyl acetate, washed with 2N-hydrochloric acid, water, and brine and dried. The residue was chromatographed over Kieselgel 60 eluting with light petroleum:ethyl acetate (4:1) to give a foam (202 mg).

A sample of the foam (20 mg) was crystallised from light petroleum (0.2 ml) to give the title compound as a colourless solid, m.p. 128°-130°, $[\alpha]_D^{21}$ +122° (c 0.43, CHCl$_3$).

EXAMPLE 8

5-Keto Factor A 23-n-propyl ether

A solution of 5-keto Factor A (611 mg) in dry ether (25 ml) was stirred at 20° under nitrogen, and silver carbonate (1.38 g), 1-iodopropane (0.6 ml) and silver perchlorate (1.036 g) were added. The resulting suspension was stirred for 3.5 h, and then kept at 20° for a further 18 h. The mixture was diluted with ethyl acetate (25 ml), then filtered through kisselguhr, and the filter bed was washed with ethyl acetate (25 ml). The filtrate and washing were combined, and washed with aqueous sodium metabisulphite, 2N-sodium hydroxide, 2N-hydrochloric acid, and brine (25 ml of each,), and dried (magnesium sulphate), and concentrated to ca. 5 ml. The resulting solution was diluted with light petroleum (ca. 5 ml), and then purified by chromatography over Kieselgel 60 (60 g). Elution of the column with light petroleum:ethyl acetate (4:1) gave a foam (385 mg), which was crystallised from light petroleum (ca. 10 ml) to provide the title compound (280 mg) as a colourless solid, m.p. 115° to 127° (decomp.), $[\alpha]_D^{20}$ +121° (c 0.65, CHCl$_3$), $\lambda_{max}$ (EtOH) 241 nm ($\epsilon$ 29,800), $\gamma_{max}$ (CHBr$_3$) 3460 (OH), 1710 (ester) and 1678 cm$^{-1}$ (enone), δ(CDCl$_3$) include 6.57 (s, 1H), 5.21 (d, J 9 Hz, 1H), 3.94 (s, 1H), 3.84(s, 1H), 3.45 (m, 1H), 3.12(dq, J 7, 10 Hz, 1H) and 0.74 (d, J 6 Hz, 3H).

EXAMPLE 9

23-Desoxy-5-keto-23-methylene Factor A

23-Desoxy-23-methylene Factor A (0.014 g) was dissolved in ethyl acetate (1 ml) and stirred with activated manganese dioxide (0.02 g) for 20 minutes. The reaction mixture was filtered through a Kieselguhr pad, and washed through with further quantities of ethyl acetate. The solution was evaporated under vacuum to give the title compound (0.011 g). δ(CDCl$_3$) includes 3.52 (m; 1H), 4.6-4.8(m; 4H) and 6.51(s; 1H).

EXAMPLE 10

5,23-Bis (methoxyimino) Factor A

A methanolic solution containing 5,23-diketo Factor A (150 mg), methoxyamine hydrochloride (280 mg) and sodium acetate (250 mg) was kept at about 20° for 20 h, and was then diluted with ether (40 ml) and ethyl acetate (20 ml) and washed successively with 2N hydrochloric acid and water. The dried organic phase was evaporated and the resultant gum was purified by chromatography over Merck Kieselgel 60 230-400 mesh (100 ml). Elution of the column with hexane:ethyl acetate (3:1) afforded the title compound as a white foam (58 mg). $[\alpha]_D^{21}+119°$(c 0.86, CHCl$_3$); $\lambda_{max}$ (EtOH) 246 nm ($\epsilon$ 29,700); $\gamma_{max}$ (CHBr$_3$) (cm$^{-1}$) 3540, 3460 (OH) 1710 C=O) 990 (C-O); $\delta$ (CDCl$_3$) include 5.7-5.9 (m; 3H), 4.56 (s; 1H), 4.00 (s; 3H), 3.82 (s; 3H), 3.30 (d15; 1H), 1.94 (s, 3H).

Examples 11 to 13 were prepared in a similar manner from methoxyamine hydrochloride and the appropriate 5-keto Factor A derivative.

EXAMPLE 11

5-Methoxyimino Factor A

5-Keto Factor A gave the title compound as a light yellow foam. $[\alpha]_D^{21}+143°$ (c 0.98, CHCl$_3$); $\lambda_{max}$ (EtOH) 246 nm ($\epsilon$ 28,900); $\gamma_{max}$ (CHBr$_3$) (cm$^{-1}$) 3490 (OH), 1708 (C=O) 992 (C-O); $\delta$(CDCl$_3$) include 5.7-5.9(m; 3H), 4.65(s; 1H), 4.01(s; 3H), 3.80(d 10, q 3; 1H), 1.94(s; 3H).

EXAMPLE 12

5-Methoxyimino Factor A 23-ethyl ether

5-Keto Factor A 23-ethyl ether gave the title compound as a light yellow foam. $[\alpha]_D^{21}+167°$ (c 1.19, CHCl$_3$); $\lambda_{max}$ (EtOH) 246 nm ($\epsilon$ 30,500); $\gamma_{max}$ (CHBr$_3$) (cm$^{-1}$) 3530, 3460 (OH), 1708 (C=O), 1000 (C-O); $\delta$ (CDCl$_3$) include 5.7-5.9 (m; 3H), 4.55 (s; 1H), 4.00 (s; 3H), 3.64 (m; 1H) 3.26 (m; 1H), 3.47 (m; 1H), 1.95 (s; 3H), 1.15 (t 7; 3H).

EXAMPLE 13

23-Desoxy-5-methoxyimino Factor A

23-Desoxy-5-keto Factor A gave the title compound as a white foam. $[\alpha]_D^{21}+140°$ (c 1.21, CHCl$_3$); $\lambda_{max}$ (EtOH) 246 nm ($\epsilon$ 27,300); $\gamma_{max}$ (CHBr$_3$) (cm$^{-1}$) 3460 (OH), 1710 (C=O) 990 (C-O); $\delta$ (CDCl$_3$) include 5.6-5.9 (m; 3H), 4.56 (s; 1H), 4.00 (s; 3H), 3.42 (broadened d 10 1H), 1.94 (s; 3H), 0.69 (d 5; 3H)

EXAMPLE 14

5-hydroxyimino Factor C

Hydroxylamine hydrochloride (135 mg) and anhydrous sodium acetate (148 mg) were stirred together in dioxan (5 ml) containing a few drops of water and one drop of glacial acetic acid. After 5 min 5-keto Factor C (170 mg) was added and the mixture stirred at 21° for 3.5 h. The mixture was next diluted with ether and the organic phase washed well with water. Evaporation of the dried organic phase gave a gum which was purified by chromatography over Sorbsil silica. Gradient elution with dichloromethane:ether (100:0 to 98:2) gave the title compound which precipitated as an amorphous solid from ether-pentane $\lambda_{max}$ (EtOH) 245 nm ($\epsilon_{max}$ 27,500); $\gamma_{max}$ (CHBr$_3$) 3130-3600 (OH), and 1708 cm$^{-1}$ (ester); $\delta$ (CDCl$_3$) include 8.61 (broad s, 1H), 5.80 (s, 1H), 4.64 (s, 1H), 1.90 (s, 3H), 1.63 (d 6 Hz, 3H), 1.57 (s, 3H), 1.49 (s, 3H), 0.96 (d 6 Hz, 3H), and 0.76 (d 6 Hz, 3H) m/z=598 (MH+).

EXAMPLE 15

5-Hydroxyimino Factor A

To a stirred mixture of hydroxylamine hydrochloride (120 mg) and anhydrous sodium acetate (131 mg) in dioxan (6 ml) containing a few drops of water and a single drop of glacial acetic acid was added 5-keto Factor A (151 mg). After stirring this mixture at room temperature for 4 h it was diluted with ether and the organic phase extracted with saturated aqueous sodium bicarbonate solution. Removal of solvent from the dried organic phase afforded a gum which in dichloromethane was introduced on to a short Sorbsil silica column made up in the same solvent. Elution with dichloromethane and then with dichloromethane-ether (98.5:1.5) provided the title compound (46 mg) obtained as an amorphous solid from ether-pentane $\lambda_{max}$ (EtOH) 245 nm ($\epsilon_{max}$ 30,700); $\gamma_{max}$ (CHBr$_3$) 3140-3600 (OH) and 1705 cm$^{-1}$ (ester); $\delta$ (CDCl$_3$) include 8.25 (broad s; 1H), 5.81 (s; 1H) 5.21 (d; 8 Hz, 1H), 4.66 (s; 1H), 2.59 (m; 1H), 1.93 (s; 3H), 1.62 (s, 3H), 1.54 (s, 3H), 1.05 (d; 6 Hz, 3H), 1.01 (d; 6 Hz; 3H), 0.96 (d; 6 Hz; 3H) and 0.81 (d; 7 Hz; 3H) m/z=625 (M+).

EXAMPLE 16

5-Keto 23 [E]-methoxyimino Factor A 5,23-Diketo Factor A (475 mg), methoxylamine hydrochloride (69 mg) and anhydrous sodium acetate (135 mg) were dissolved in methanol. After 1.5 h at room temperature, the solution was kept at −18° for 16 h, diluted with ethyl acetate and washed successively with 1N hydrochloric acid, water, and brine. The dried organic phase was evaporated and the yellow foam was purified by chromatography over Merck Keiselgel 60, 230 to 400 mesh (120 ml). Elution of the column with hexane:ethyl acetate (4:1) afforded the title compound as a yellow foam (255 mg) $[\alpha]_D<+80°$ (c 1.20, CHCl$_3$), $\lambda_{max}$ (EtOH) 241 nm ($\epsilon$ 27,500), $\gamma_{max}$ (CHBr$_3$), 3530, 3460 (OH) 1708 (C=O), 1676 (C=C-C=O), 986 (C-O), $\delta$ (CDCl$_3$) include 6.58 (s; 1H), 3.84 (s; 4H), 3.80 (s; 1H), 3.58 (m; 1H), 3.30 (d14; 1H), 1.00 (d6; 3H), 0.96 (d6; 3H), 0.92 (d6; 3H).

EXAMPLE 17

5-Hydroxyimino Factor D

A solution of 5-keto Factor D (278 mg) in dry pyridine (2.5 ml) was treated with hydroxylamine hydrochloride monohydrate (45 mg) added in one portion. After stirring for 5 hr at 21° the yellow solution was poured into dichloromethane (20 ml) and was then washed successively with 2N hydrochloric acid, water and brine. Drying and evaporation yielded a yellow foam (298 mq). Purification of the foam by column chromatography using Merck Kieselgel 60, 70-230 mesh silica (35 g) and dichloromethane: acetone (35:1) as eluent afforded one major component (138 mg). Further purification of this solid by preparative reverse-phase HPLC gave the title compound as a solid (79 mg) after trituration with pentane, m.p. 162°-164°, $[\alpha]_D^{21}+87°$ (c 0.55, CHCl$_3$), $\lambda_{max}^{EtOH}$ 245 nm ($\epsilon_{max}$ 30,500); $\gamma_{max}$ (CHBr$_3$) 3530 and 3490 (OH) and 1710 cm$^{-1}$ (C=O); $\delta$(CDCl$_3$) 0.81 (d, 7 Hz; 3H), 1.00 (d, 6 Hz; 3H), 1.01 (d, 7 Hz; 3H), 1.53 (s; 3H), 1.60 (s; 3H), 1.93 (s; 3H), 3.39 (m; 1H) and 4.66 (s; 1H). m/z=611 (M+).

EXAMPLE 18

5-Methoxyimino 23-keto Factor A

5-Methoxyimino Factor A was oxidised by pyridinium dichromate in dry N,N-dimethylformamide at ambient temperature by the method described in GB 2176182A. Purification by chromatography over Merck Keiselgel 60, 230-400 mesh, eluting with hexane:ethyl acetate (3:1) afforded the title compound as a tan foam (47 mg), $\lambda_{max}$ (EtOH) 246 nm ($\epsilon$ 29,100) $\gamma_{max}$ (CHBr$_3$) (cm$^{-1}$) 1710 (C=O), 1050, 1025 (C-O), $\delta$(CDCl$_3$) include 5.7–5.9 (m; 3H), 4.55 (s; 3H), 4.01 (s; 3H), 2.51 (s; 2H), 1.96 (s; 3H), 1.70 (s; 3H), 1.51 (s; 3H), 1.07 (d6; 3H), 1.00 (d6; 3H), 0.97 (d6; 3H) and 0.87 (d6; 3H).

The following are examples of formulations according to the invention. The term 'Active Ingredient' as used hereinafter means a compound of the invention.

| Multidose parenteral injection | | |
|---|---|---|
| | % w/v | Range |
| Active Ingredient | 4.0 | 0.1–7.5% w/v |
| Benzyl alcohol | 2.0 | |
| Glyceryl triacetate | 30.0 | |
| Propylene glycol to | 100.0 | |

Dissolve the active ingredient in the benzyl alcohol and glyceryl triacetate. Add propylene glycol and make up to volume. Sterilise the product by conventional pharmaceutical methods, for example sterile filtration or by heating in an autoclave and package aseptically.

| Aerosol spray | | |
|---|---|---|
| | % w/w | Range |
| Active Ingredient | 0.1 | 0.01–2.0% w/w |
| Trichloroethane | 29.9 | |
| Trichlorofluoromethane | 35.0 | |
| Dichlorodifluoromethane | 35.0 | |

Mix the Active Ingredient with trichloroethane and fill into the aerosol container. Purge the headspace with the gaseous propellant and crimp the valve into position. Fill the required weight of liquid propellant under pressure through the valve. Fit with actuators and dust-caps.

| Tablet Method of manufacture-wet granulation | |
|---|---|
| | mg |
| Active Ingredient | 250.0 |
| Magnesium stearate | 4.5 |
| Maize starch | 22.5 |
| Sodium starch glycolate | 9.0 |
| Sodium lauryl sulphate | 4.5 |

Microcrystalline cellulose to tablet core weight of 450 mg Add sufficient quantity of a 10% starch paste to the active ingredient to produce a suitable wet mass for granulation. Prepare the granules and dry using a tray or fluid-bed drier. Sift through a seive, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

| Veterinary tablet for small/domestic animal use Method of manufacture-dry granulation | |
|---|---|
| | mg |
| Active Ingredient | 50.0 |
| Magnesium stearate | 7.5 |
| Microcrystalline cellulose to tablet | 75.0 |

-continued

| Veterinary tablet for small/domestic animal use Method of manufacture-dry granulation | |
|---|---|
| | mg |
| core weight of | |

Blend the active ingredient with the magnesium stearate and microcrystalline cellulose. Compact the blend into slugs. Break down the slugs by passing through a rotary granulator to produce free-flowing granules. Compress into tablets.

The tablet cores can then be film-coated, if desired, as described above.

| Veterinary intrammary injection | | | |
|---|---|---|---|
| | | mg/dose | Range |
| Active Ingredient | | 150 mg | 0.05–1.0 g |
| Polysorbate 60 | 3.0% w/w | to 3 g | to 3 or 15 g |
| White Beeswax | 6.0% w/w | | |
| Arachis oil | 91.0% w/w | | |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

| Veterinary oral drench | | |
|---|---|---|
| | % w/v | Range |
| Active Ingredient | 0.35 | 0.01–2% w/v |
| Polysorbate 85 | 5.0 | |
| Benzyl alcohol | 3.0 | |
| Propylene glycol | 30.0 | |
| Phosphate buffer | as pH 6.0–6.5 | |
| Water | to 100.0 | |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

| Veterinary oral paste | | |
|---|---|---|
| | % w/w | Range |
| Active Ingredient | 7.5 | 1–30% w/w |
| Saccharin | 25.0 | |
| Polysorbate 85 | 3.0 | |
| Aluminium distearate | 5.0 | |
| Fractionated coconut oil | to 100.0 | |

Disperse the aluminum distearate in the fractionated coconut oil and polysorbate 85 by heating. Cool to room temperature and disperse the saccharin in the oily vehicle. Dispense the active ingredient in the base. Fill into plastic syringes.

| Granules for veterinary in-feed administration | | |
|---|---|---|
| | % w/w | Range |
| Active Ingredient | 2.5 | 0.05–5% w/w |
| Calcium sulphate, hemi-hydrate | to 100.0 | |

Blend the Active Ingredient with the calcium sulphate. Prepare the granules using a wet granulation process. Dry using a tray or fluid-bed drier. Fill into the appropriate container.

| Emulsifiable Concentrate | |
|---|---|
| Active ingredient | 50 g |
| Anionic emulsifier | 40 g |
| (e.g. Phenyl sulphonate CALX) | |
| Non-ionic emulsifier | 60 g |
| (e.g. Syperonic NP13) | |
| Aromatic solvent (e.g. Solvesso 100) to 1 liter. | |

Mix all ingredients, stir until dissolved.

| | Granules | |
|---|---|---|
| (a) | Active ingredient | 50 g |
| | Wood resin | 40 g |
| | Gypsum granules (20-60 mesh) to 1 kg | |
| | (e.g. Agsorb 100A) | |
| (b) | Active ingredient | 50 g |
| | Syperonic NP13 | 40 g |
| | Gypsum granules (20-60 mesh) to 1 kg. | |

Dissolve all ingredients in a volatile solvent e.g. methylene chloride, add to granules tumbling in mixer. Dry to remove solvent.

We claim:
1. A compound of formula (I)

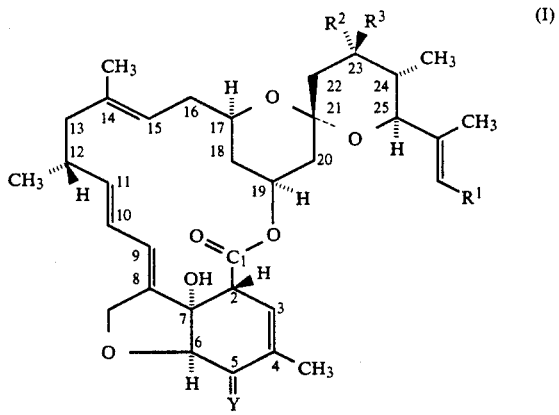

wherein
$R^1$ is a methyl, ethyl or isopropyl group;
$R^2$ is a hydrogen atom and $R^3$ is a bromine; and
Y represents an oxygen atom or a group $NOR^5$ and $R^5$ is a hydrogen atom, a $C_{1-8}$ alkyl group or a $C_{3-8}$ alkenyl group.

* * * * *